Jan. 15, 1974 A. BOHLS Plant Pat. 3,434

PECAN TREE

Filed May 4, 1972

United States Patent Office

Plant Pat. 3,434
Patented Jan. 15, 1974

3,434

PECAN TREE

Allie Bohls, Austin, Tex., assignor to
O. S. Gray, Arlington, Tex.

Filed May 4, 1972, Ser. No. 250,446
Int. Cl. A01h 5/03
U.S. Cl. Plt.—31 1 Claim

ABSTRACT OF THE DISCLOSURE

A new variety of pecan tree distinguished by its vigorous, spreading and twiggy growth habit and by its precocious and prolific production of thin shelled nuts having a high weight ratio of kernel to shell.

BACKGROUND OF THE INVENTION

This new variety of pecan tree originated as a seedling of unknown parentage selected from among many seedlings resulting from a considerable number of cross-pollinations between various known varieties of pecan trees growing in the pecan grove located on applicant's ranch bordering the Colorado River and about 12 miles west of Austin, Tex. For many years, applicant had sought to produce improved varieties of pecan trees by cross-pollinating selected ones of the various producing varieties growing on his ranch and the new variety herein disclosed is the result of one of his numerous crosses.

This seedling was selected for propagation because of its vigorous and unusually twiggy growth, its precocious and prolific production of nut clusters, and because the mature nuts exhibited a much improved cracking quality with a very high ratio of kernel weight compared to the weight of the whole nut. Asexual propagation of this selected seedling was carried on by applicant at his pecan grove by both budding and grafting and all of the resulting plants have reproduced the favorable characteristics of the original in all respects, both as to growth habit of the tree and the outstanding qualities of the nut.

DESCRIPTION OF THE NEW TREE

Figure 1:
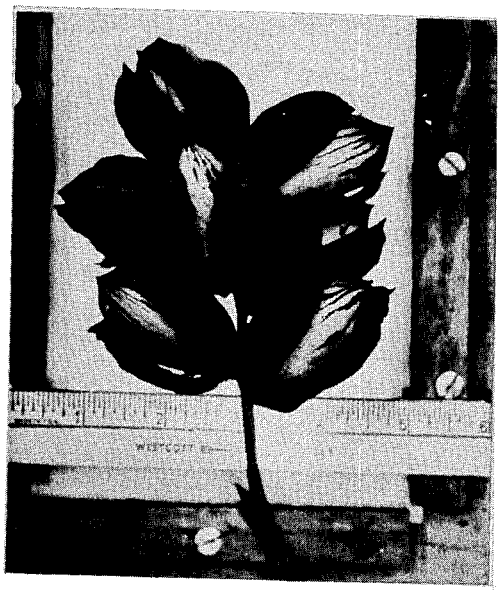
FIG. 1 is a view showing a ripened nut cluster.
Figure 2:
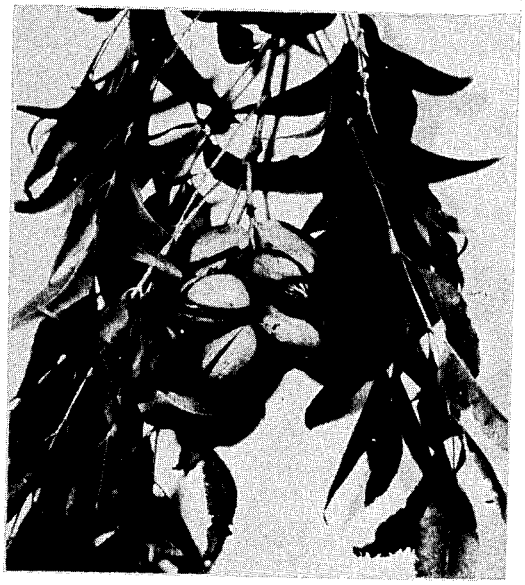
FIG. 2 is a view showing foliage and a twig bearing a nut cluster.
Figure 3:
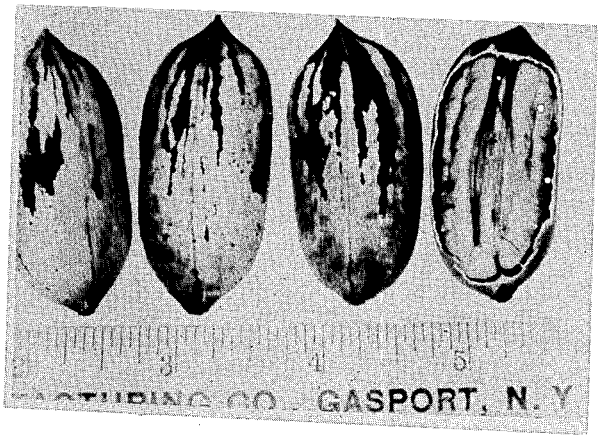
FIG. 3 is a view showing nuts of the new variety of pecan tree, one of the nuts being broken open to show the kernel and thickness of the shell.

Growth habit: The new tree is vigorous and spreading in its growth habit producing many branches which form numerous slender bearing-branches or twigs and result in a prolific production of nut clusters, which very often contain 7 to 9 nuts. The new tree begins bearing at a very early age and often produces nuts the second summer after grafting.

Foliage: The leaves of this tree are in normal abundance for pecan trees and are of odd-pinnate compound form with 13 to 19 leaflets. The leaflets are somewhat lanceolate, typically long, narrow and tapering to an acuminate tip. Under normal conditions, the leaflets measure about one inch in width and approximately four inches long.

Buds: The buds of this new variety of pecan tree are typically closely spaced on the twigs or branches, approximately ¾ to 1 inch apart, permitting the formation of numerous fruiting shoots and producing relatively large clusters of nuts. Bud shape is generally ovate.

Flowers: Flowers appear in early Spring and both staminate and pistillate flowers are produced in the usual manner on the same tree. The flowers begin to form very early in the life of this tree and this precocious habit is a distinguishing characteristic of the new variety. This tree is a protogynous bloomer, its pistillate flowers becoming receptive before its pollen begins to shed.

Nuts:

*Ripening habit.*—Even and slightly earlier than mid-season, with the ripe nuts separating easily from the shucks when harvested.

*Quantity.*—Prolific production of large nut clusters resulting in an exceptionally heavy crop, each nut cluster usually having 4 or 5 nuts and many clusters having 7 to 9 nuts.

*Size and shape.*—Medium to large in size, measuring 1⅞ inches long and ⅞ inch across the shoulder, counting 38 or 39 nuts per pound under good growing conditions. Under normal conditions, the count will be about 45 nuts per pound. The nut shape is generally cylindrical with a pointed apex and tapering slightly toward the base which is bluntly pointed.

*Color.*—Light tan with a scattering of dark brown pinpoint size dots and with dark brown irregularly shaped stripes tinged with purple extending lengthwise along the apical half.

*Shell and husk.*—Both shell and husk are exceptionally thin, averaging only about one-half the thickness of the shell and husk of the best known and widely grown Stuart variety (unpatented).

*Cracking quality.*—A small amount of space between the shell and kernel permits easy cracking by hand or machine without crushing the kernel, resulting in an exceptionally high percentage of whole half-kernels.

*Kernels.*—Light golden brown in color and of good flavor. Wide primary and less prominent secondary grooves, extending lengthwise of the dorsal sides of the kernels, release the "cork" readily when the nuts are cracked and the kernel halves release easily from the septum that divides them.

*Shelling quality.*—The unusually thin shell of the nut results in a very high kernel weight compared to the total weight of the nut. Cracking tests show 60 to 61 pounds of kernels resulting from each 100 pounds of whole nuts and selected nuts have yielded as high as 66% kernel.

Disease resistance: This pecan tree and the nuts therefrom are susceptible to scab disease to about the same extent as the well known "Mahan" and "Western" varieties growing in the same area. The natural adaptation of this new variety is for the drier atmosphere of the Southwestern part of the United States and when grown in more humid regions, it will be necessary to spray the trees for control of scab disease.

This new variety of pecan tree is particularly distinguished by its precocious bearing habit and its prolific production of thin shelled, medium to large nuts having a very high kernel to shell weight ratio. Other advantageous and distinguishing characteristics reside in the spreading growth habit which provides numerous small, twiggy terminal branches toward the ends of the larger limbs whereby more numerous nut clusters are produced; and the nuts produced by this tree are clean looking with a unique light tan color and a distinctive striping pattern.

I claim:

1. A new variety of pecan tree substantially as herein shown and described, characterized by its precocious bearing and prolific production of medium to large sized and very thin shelled nuts, and by the very high weight percentage of the nut meat compared to the weight of the whole nut.

No references cited.

ROBERT E. BAGWILL, Primary Examiner